United States Patent
Mongenet et al.

(10) Patent No.: US 6,274,771 B1
(45) Date of Patent: *Aug. 14, 2001

(54) CONTINUOUS PROCESS FOR THE MANUFACTURE OF 3,5,5-TRIMETHYLCYCLOHEXA-3-EN-1-ONE (B-ISOPHORONE)

(75) Inventors: Francois Mongenet, Chuzelles; Rémy Teissier, Francheville, both of (FR)

(73) Assignee: Atofina, Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/598,484

(22) Filed: Jun. 22, 2000

(30) Foreign Application Priority Data

Jun. 22, 1999 (FR) .................................................. 9907919

(51) Int. Cl.$^7$ .................................................. C07C 45/67
(52) U.S. Cl. .............................................................. 568/341
(58) Field of Search ..................................... 568/341, 343

(56) References Cited

U.S. PATENT DOCUMENTS 4,845,303 * 7/1989 Bellut .
5,276,197 * 1/1994 Nosberger et al. .
5,907,065 * 5/1999 Krill et al. .

FOREIGN PATENT DOCUMENTS

| 0 832 871 A1 | 4/1998 | (EP) . |
| 0 842 918 A1 | 5/1998 | (EP) . |
| 2 253 730 | 7/1995 | (FR) . |

* cited by examiner

*Primary Examiner*—Sreeni Padmanabhan
*Assistant Examiner*—Sikarl A. Witherspoon
(74) *Attorney, Agent, or Firm*—Millen, White, Zelano & Branigan, P.C.

(57) ABSTRACT

For the continuous manufacture of β-isophorone by isomerization under homogeneous catalysis of α-isophorone, the steps of introducing the α-isophorone and a solution of an alkaline hydroxide into a reaction region, bringing the reaction mixture to reflux at a temperature at least equal to 150° C. under a equal P1 of less than or equal to atmospheric pressure, continuously and simultaneously removing from the reaction mixture: β-isophorone vapor, by distillation under a pressure P2 less than P1 and at a temperature at most equal to 150° C., and heavy products, at a rate, so that their content by weight is at most equal to 7% in the reaction mixture, and continuous returning the distillation to the reaction region.

21 Claims, 1 Drawing Sheet

CONTINUOUS PROCESS FOR THE MANUFACTURE OF 3,5,5-TRIMETHYLCYCLOHEXA-3-EN-1-ONE (Β-ISOPHORONE)

CROSS-REFERENCE TO RELATED APPLICATION

This application is related to Applicants' concurrently filed application entitled "Continuous Process For The Manufacture Of 3,5,5-Trimethylcyclohexa-3-EN-1-One (β-Isophorone)", based on French Application 99/07.920 filed Jun.22, 1999.

FIELD OF INVENTION

The invention relates to a continuous process for the manufacture of 3,5,5-trimethylcyclohexa-3-en-1-one, hereinafter β-isophorone, by isomerization of 3,5,5-trimethylcyclohexa-2-en-1-one, hereinafter α-isophorone, in the liquid phase in the presence of a homogeneous catalyst.

BACKGROUND OF THE INVENTION

β-Isophorone is a synthetic intermediate in the manufacture of carotenoids, of vitamins, such as vitamin E, and of pharmaceuticals.

It is also directly involved in syntheses of fragrances and natural products, such as astaxanthin and abscisic acid and derivatives.

β-Isophorone is an isomer of α-isophorone, obtained by trimerization of acetone in alkaline medium, which is distinguished from the latter by the position of the double bond: the double bond is no longer conjugated with the carbonyl, as represented hereinbelow:

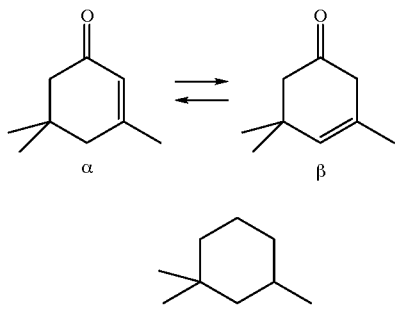

The isomerization of α-isophorone to β-isophorone is an equilibrium deconjugation reaction of the double bond and of the carbonyl and, for this reason, the thermodynamic equilibrium is weighted towards α-isophorone.

Numerous processes for the isomerization of α-isophorone to β-isophorone have been described but exhibit numerous disadvantages, such as high consumption of chemicals (in particular catalysts), mediocre yields or formation of α-isophorone condensation products (heavy products), which results in a rise in the temperature of the reaction mixture, thus accelerating the formation of heavy products, which destabilize the system.

Patent EP 832,871, Example 7, discloses a process for the preparation of β-isophorone by catalytic isomerization of α-isophorone which consists, in a first step, in continuously extracting from the reaction mixture, by distillation, a primary mixture comprising from 20 to 22% of β-isophorone and in then isolating from this mixture, by distillation, a β-isophorone with a purity equal to approximately 98%. It is found, when proceeding in this way, that a mixture composed of approximately 90% of α-isophorone and 10% of heavy products is collected in the recirculation evaporator. In view of the duration of operation (approximately 15 hours) and of the amount of product collected in the said evaporator (615 g), this corresponds to an hourly production of heavy products of approximately 4 g/h.

In addition, a large amount by weight of catalyst is used: 0.6% with respect to the α-isophorone employed.

If the thermodynamics of the reaction are considered, it is found that the temperature at which isomerization is carried out fixes the concentration of β-isophorone at equilibrium: the higher the temperature, the greater the concentration at equilibrium of β-isophorone. As β-isophorone is more volatile than α-isophorone, the equilibrium can be shifted by distillation of the most volatile product. In addition, β-isophorone, on heating at a temperature of greater than 150° C., reverse isomerizes to α-isophorone, even in the absence of catalyst: the kinetics of this thermal reverse isomerization are controlled by the temperature level.

Furthermore, to carry out the isomerization, it is necessary to pass through the intermediate enol or enolate, which are also intermediates of the aldolization/crotonization reaction, which results in the formation of isophorone polycondensates which constitute heavy products, the formation of which is to be prohibited since they represent a loss of isophorone in a process for the manufacture of β-isophorone. The formation of the heavy products is promoted, on the one hand, by the concentration of catalyst and, on the other hand, by the temperature.

Thus, the use of heterogeneous catalysis does not appear to be very favourable as it can increase the concentration of heavy products at the surface of the solid catalyst, which can deactivate the said catalyst.

SUMMARY OF THE INVENTION

A continuous process for the manufacture of 3,5,5-trimethylcyclohexa-3-en-1-one (β-isophorone) by isomerization under homogeneous catalysis of 3,5,5-trimethylcyclohexa-2-en-1-one (α-isophorone), obtained by trimerization of acetone in alkaline medium, has now been found, the said process being characterized in that the following stages are carried out:

a) α-isophorone and a solution of an alkaline hydroxide are continuously introduced into a reaction region, b) the reaction mixture is brought to reflux at a temperature at least equal to 150° C., preferably at a temperature ranging from 190° C. to 216° C., and under a pressure P1 of less than or equal to atmospheric pressure, c) the following are continuously and simultaneously removed from the reaction mixture:
 1) the β-isophorone of the vapour phase, by distillation under a pressure P2 which is less than P1 and at a temperature at most equal to 150° C.,
 2) heavy products, by drawing off, so that their content by weight is at most equal to 7% in the reaction mixture, and d) the distillation condensates are continuously returned to the reaction region.

According to the present invention, the pressure P1 is between 150 mbar and atmospheric pressure and the pressure P2, which is less than P1, is at most equal to 150 mbar and, preferably, between 50 mbar and 100 mbar.

According to the present invention, the alkaline hydroxide is NaOH or KOH. It is preferable to use KOH. This alkaline hydroxide can be dissolved in water or an aliphatic alcohol of low molecular weight, such as methanol, ethanol, propanol or isopropanol. Methanol or ethanol is generally used.

According to the present invention, use is made of an amount by weight of alkaline hydroxide at most equal to 0.03% with respect to the α-isophorone introduced into the reaction region.

Use will preferably be made of an amount by weight of alkaline hydroxide ranging from 0.010% to 0.020%.

The reflux ratio for the distillation of the fraction comprising the β-isophorone, the parameter which regulates the purity of this fraction, is chosen so as to obtain a high β-isophorone productivity, that is to say to minimize the thermal retrogression, for a maximum β-isophorone purity.

According to the invention, a mixture comprising a percentage by weight of heavy products at most equal to 7%, the remainder being a mixture of α- and β-isophorones, is continuously extracted. These heavy products are composed essentially of dimers and trimers of isophorone and also of catalytic residues. These heavy products can advantageously be introduced into a line for the manufacture α-isophorone by basic catalysis, after the trimerization reaction of acetone and before the neutralization of the basic catalyst.

The continuous process according to the present invention, characterized by continuously drawing off the heavy products, exhibits the advantage, by limiting the concentration of the said heavy products in the boiler, of stabilizing the temperature of the isomerization.

Another advantage of the process of the invention is that it is not necessary to carry out expensive treatment operations on the said heavy products since they can be recycled in a unit for the manufacture of α-isophorone.

The process of the invention also exhibits the advantage of consuming small amounts of catalytic charge.

DESCRIPTION OF THE DRAWING

The process can be carried out in equipment as represented diagrammatically in FIG. 1 which is composed of:
- a boiler (1), in which the isomerization reaction of α-isophorone to β-isophorone is carried out, surmounted by an adiabatic column (2) which can comprise a packing, such as Sulzer EX20, and which is equipped with a distillation column top comprising a timer which makes it possible to regulate the reflux ratio; the reflux ratio R being defined as being the ratio of the total amount of condensate obtained at the distillation column top to the amount of product extracted.

The boiler (1) is equipped with heating means not represented in FIG. 1.

Figure 1:
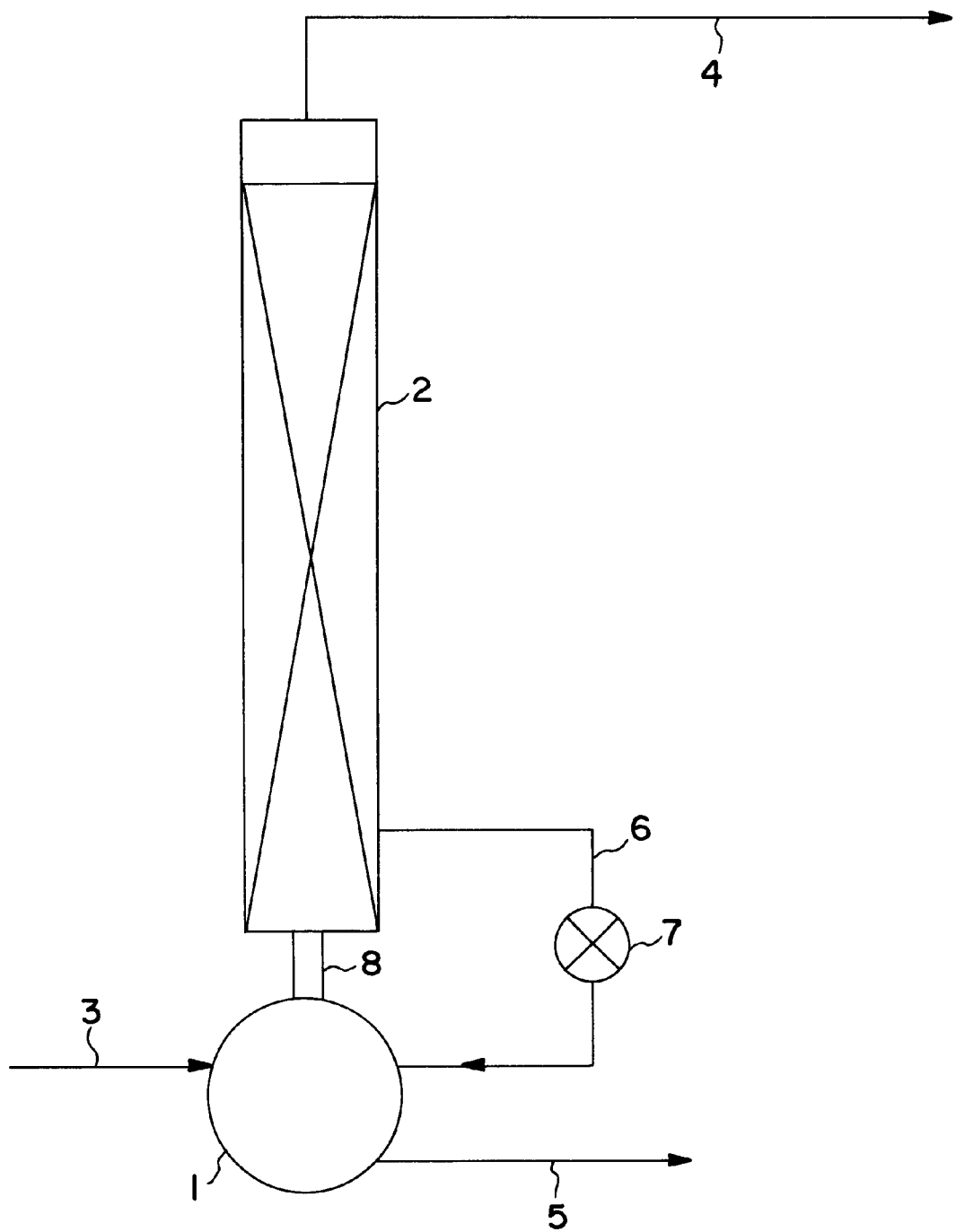

The boiler (1) is fed via the line (3), the β-isophorone is recovered via the line (4) and the heavy products extracted from the boiler are drawn off via the line (5).

The condensates are withdrawn at the bottom of the column (2) and returned to the boiler (1) via the line (6) equipped with a pump (7).

A pressure-reduction device (8) is inserted between the boiler (1) and the column (2).

The dimensions of the column and of the boiler are calculated according to the amount of α-isophorone to be isomerized and to the desired productivity and are part of the general knowledge of a person skilled in the art.

The test hereinbelow was carried out in laboratory equipment by way of illustration of the present invention.

A boiler composed of a 1 liter glass reactor comprises 300 grams of a mixture composed of α-isophorone comprising 0.02% by weight of KOH (expressed as pure KOH) dissolved beforehand in methanol at a concentration by weight of KOH equal to approximately 20%.

This mixture is heated to 196° C. under a pressure of 600 mbar. The vapours are continuously injected into an adiabatic column, comprising a Sulzer EX20 stacked packing made of 316L stainless steel, under a pressure of 100 mbar. The temperature at the column top stabilizes at 110° C.–111° C.

A β-isophorone with a purity, defined as being the β-isophorone/α-isophorone ratio, of greater than 99% is extracted for a reflux ratio R of 60.

The extraction throughput stabilizes at 4 g/hour.

The distillation condensates are conveyed to the boiler using a pump.

The test lasts 10 hours.

The heavy products are continuously extracted.

The extraction of the said heavy products and the production of β-isophorone are compensated for by introduction of α-isophorone with the catalyst.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.919, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A continuous process for the manufacture of 3,5,5-trimethylcyclohexa-3-en-1-one (β-isophorone) by isomerization under homogeneous catalysis of 3,5,5-trimethylcyclohexa-2-en-1-one (α-isophorone), obtained by trimerization of acetone in alkaline medium, the said process being characterized in that the following stages are carried out:
   a) α-isophorone and a solution of an alkaline hydroxide are continuously introduced into a reaction region,
   b) the reaction mixture is brought to reflux at a temperature at least equal to 150° C. and under a pressure P1 of less than or equal to atmospheric pressure,
   c) the following are continuously and simultaneously removed from the reaction mixture:
      1) the β-isophorone of the vapour phase, by distillation under a pressure P2 which is less than P1 and at a temperature at most equal to 150° C.,
      2) heavy products, by drawing off, so that their content by weight is at most equal to 7% in the reaction mixture, and
   d) the distillation condensates are continuously returned to the reaction region.

2. A process according to claim 1, characterized in that the pressure P1 is between 150 mbar and atmospheric pressure and the pressure P2, which is less than P1, is at most equal to 150 mbar.

3. A process according to claim 2, characterized in that the pressure P2 is between 50 mbar and 100 mbar.

4. A process according to claim 1, characterized in that, in stage b), the reaction mixture is brought to a temperature ranging from 190° C. to 216° C.

5. A process according to claim 1, characterized in that the alkaline hydroxide is KOH.

6. A process according to claim 1, characterized in that the alkaline hydroxide is dissolved in an aliphatic alcohol of low molecular weight.

7. A process according to claim 6, characterized in that the aliphatic alcohol of low molecular weight is methanol or ethanol.

8. A process according to claim 1, characterized in that use is made of an amount by weight of alkaline hydroxide at most equal to 0.03% with respect to the α-isophorone employed.

9. A process according to claim 8, characterized in that use is made of an amount by weight of alkaline hydroxide ranging from 0.010% to 0.020% with respect to the α-isophorone employed.

10. A process according to claim 2, characterized in that use is made of an amount by weight of alkaline hydroxide at most equal to 0.03% with respect to the α-isophorone employed.

11. A process according to claim 3, characterized in that use is made of an amount by weight of alkaline hydroxide at most equal to 0.03% with respect to the α-isophorone employed.

12. A process according to claim 2, characterized in that use is made of an amount by weight of alkaline hydroxide ranging from 0.010% to 0.020% with respect to the α-isophorone employed.

13. A process according to claim 3, characterized in that use is made of an amount by weight of alkaline hydroxide ranging from 0.010% to 0.020% with respect to the α-isophorone employed.

14. A process according to claim 13, characterized in that, in stage b), the reaction mixture is brought to a temperature ranging from 190° C. to 216° C.

15. A process according to claim 1, characterized in that the heavy products drawn off from the isomerization reactor, stage c) 2), are recycled to a process for the manufacture of α-isophorone comprising the steps of trimerizing acetone with a basic catalyst and then neutralizing the basic catalyst.

16. A process according to claim 15, characterized in that the heavy products are introduced into a process for the manufacture of α-isophorone after the trimerization reaction of the acetone and before the neutralization of the basic catalyst.

17. A continuous process according to claim 1, wherein the beta-isophorone is subjected to distillation in only one single column, and purified β-isophorone is removed at a top section of said single column, and said distillation condensates are removed from a bottom section of said single column and returned to said reaction region.

18. A continuous process for the manufacture of 3,5,5-trimethylcyclohexa-3-en-one (β-isophorone) by isomelization under homogeneous catalysis of 3,5,5-trimethylcyclohexa-2-en-1-one (α-isophorone), obtained by trimerization of acetone in alkaline medium, said process comprising:

(a) continuously introducing α-isophorone and a solution of an alkaline hydroxide into a reaction region, (b) bringing the resultant reaction mixture to reflux at a temperature of at least 150° C. and under a pressure P1 of not more than atmospheric pressure, (c) continuously and simultaneously removing from the resultant refluxed reaction mixture:

(1) a gaseous mixture of β-isophorone and α-isophorone, and (2) heavy products at a rate sufficient to maintain the concentration of said heavy products in the reaction mixture at not more than 7% by weight, and (d) passing said gaseous mixture of α-isophorone and β-isophorone through a pressure-reduction device and then into a bottom section of a single distillation column, maintaining a sufficient reflux ratio in said distillation column so as to obtain a desired purity of β-isophorone at a top section of said column, and (e) withdrawing liquid condensate from the bottom of said distillation column and recycling said liquid to the reaction region, said distillation column being operated under a pressure P2 which is less than P1 and at a temperature at most equal to 150° C.

19. A process according to claim 18, wherein the alkaline hydroxide is KOH.

20. A process according to claim 18, wherein the heavy products drawn off from the isomerization reactor, stage c) 2), are recycled to a process for the manufacture of α-isophorone comprising the steps of trimerizing acetone with a basic catalyst and then neutralizing the basic catalyst.

21. A process according to claim 18, characterized in that the heavy products are introduced into a process for the manufacture of α-isophorone after the trimerization reaction of the acetone and before the neutralization of the basic catalyst.

\* \* \* \* \*